United States Patent
Suzuki et al.

(10) Patent No.: US 9,650,415 B2
(45) Date of Patent: May 16, 2017

(54) URIC ACID-LOWERING AGENT

(71) Applicant: Suntory Holdings Limited, Osaka-shi, Osaka (JP)

(72) Inventors: Toshihide Suzuki, Kizugawa (JP); Shinya Fukizawa, Kyoto (JP); Yoshinori Beppu, Jouyo (JP); Hiroshi Watanabe, Nara (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 0 days.

(21) Appl. No.: 14/787,677

(22) PCT Filed: Jun. 20, 2014

(86) PCT No.: PCT/JP2014/066424
§ 371 (c)(1),
(2) Date: Oct. 28, 2015

(87) PCT Pub. No.: WO2015/194034
PCT Pub. Date: Dec. 23, 2015

(65) Prior Publication Data
US 2016/0159858 A1  Jun. 9, 2016

(51) Int. Cl.
*A61K 38/05* (2006.01)
*C07K 5/12* (2006.01)
(Continued)

(52) U.S. Cl.
CPC ........ *C07K 5/06078* (2013.01); *A61K 38/011* (2013.01); *A61K 38/05* (2013.01);
(Continued)

(58) Field of Classification Search
CPC .... A61K 31/495; A61K 31/496; A61K 38/05; A61K 38/44; C07K 5/12
See application file for complete search history.

(56) References Cited

U.S. PATENT DOCUMENTS

| | | | |
|---|---|---|---|
| 7,214,673 B2 | 5/2007 | Aicher et al. | |
| 2002/0052381 A1* | 5/2002 | Bar-Or | A61K 31/495 514/254.05 |
| 2005/0119177 A1* | 6/2005 | Bar-Or | A61K 31/495 424/185.1 |

FOREIGN PATENT DOCUMENTS

| JP | 2006-111541 A | 4/2006 |
|---|---|---|
| JP | 20120517998 A | 8/2012 |

(Continued)

OTHER PUBLICATIONS

Chen et al. The effects of diketopiperazines from *Callyspongia* sp. on release of cytokines and chemokines . . . Bioorganic & Medicinal Chemistry Letters. 2012, vol. 22, pp. 3177-3180.*

(Continued)

*Primary Examiner* — Jeffrey E Russel
(74) *Attorney, Agent, or Firm* — Westerman, Hattori, Daniels & Adrian, LLP (57) ABSTRACT

A uric acid-lowering agent containing, as an active ingredient, a tyrosine-containing cyclic dipeptide selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or a salt thereof. The uric acid-lowering agent of the present invention has an excellent action of lowering a uric acid level, and the uric acid-lowering agent is useful in, for example, prevention or treatment of hyperuricemia, gout or the like.

16 Claims, 4 Drawing Sheets (51) Int. Cl.
  C07K 5/065    (2006.01)
  A61K 38/01    (2006.01)
  C07K 5/062    (2006.01)
  A61K 38/00    (2006.01)

(52) U.S. Cl.
  CPC ............ *C07K 5/06026* (2013.01); *C07K 5/12* (2013.01); *A61K 38/00* (2013.01)

(56) References Cited

FOREIGN PATENT DOCUMENTS

JP          2013-53115 A         3/2013
WO          2009/093141 A2       7/2009
WO       WO 2014/200000 A1  *  12/2014

OTHER PUBLICATIONS

Kutzing et al. Altered Uric Acid Levels and Disease States. The Journal of Pharmacology and Experimental Therapeutics. 2008, vol. 324, No. 1, pp. 1-7.*
Puig et al. Clinical and biochemical aspects of uric acid overproduction. Pharmacy World & Science. 1994, vol. 16, No. 2, pp. 40-54.*
Smelcerovic et al. Cyclodidepsipeptides with a promising scaffold in medicinal chemistry. Amino Acids. 2014, vol. 46, pp. 825-840.*
Alice b. Nongoierma, et al., "Tryptophan-containing milk protein-derived dipeptides inhibit xanthine oxidase", Peptides, 2012, 37(2), pp. 263-272.
Japanese Office Action dated Nov. 20, 2014 issued in counterpart Japanese patent application No. 2014-545991.
Chandan Prasad, "Bioactive Cyclic Dipeptides", Peptides, 16(1), pp. 151-164, (1995).
Hiroshi Kanzaki, "Production of novel bioactive compounds by cyclic dipeptide dehydrogenase" Biosciences and Industries, 60(7), pp. 454-457, (2002).
Alan D Borthwick, "2,5-Diketopiperazines: Synthesis, Reactions, Medicinal Chemistry, and Bioactive Natural Products", Chemical Reviews, vol. 112, (7), pp. 3641-3716, (2012).
Ayaka Takatsu, et al., "Assessment of Antioxidant Activity of Cyclic Dipeptides from Fermented Food Microorganisms and Their Related Compounds", Summary of Lecture, Annual Meeting of the Japan Society for Bioscience, Biotechnology and Agrochemistry, (2012).
International Search Report dated Aug. 19, 2014 issued in counterpart International patent application No. PCT/JP2014?066424. (2 pages).
Anika Kremer and Shu-Ming Li, "A tyrosine O-prenyltransferase catalyses the first pathway-specific step in the biosynthesis of sirodesmin PL", Microbiology (2010), 156 278-286 (cited in Korean Office Action; 9 pages; in English).
Office Action, with mailing date of Jan. 11, 2017 issued in counterpart Korean patent application No. 10-2015-7031132, with English machine translation (9 pages).

* cited by examiner

URIC ACID-LOWERING AGENT

TECHNICAL FIELD

The present invention relates to a uric acid-lowering agent. More specifically, the present invention relates to a uric acid-lowering agent, containing a cyclic dipeptide as an active ingredient; a uric acid-lowering agent containing, as an active ingredient, a composition containing the cyclic dipeptide; a composition for lowering a uric acid level, containing the cyclic dipeptide; a xanthine oxidase inhibitor containing the cyclic dipeptide as an active ingredient; a xanthine oxidase inhibitor containing, as an active ingredient, a composition containing the cyclic dipeptide; and a composition for inhibiting a xanthine oxidase containing the cyclic dipeptide.

BACKGROUND ART

"Dipeptides" in which two amino acids are bonded have been remarked as functional materials. The dipeptides make it possible to add a physical property not found in a single amino acid, or add a new function, so that the dipeptides have been expected to have a wider range of applications beyond the amino acids. Among them, diketopiperazines, which are cyclic dipeptides, have been known to have various physiological activities, and it has been expected that the diketopiperazines will expand in demands in the fields of medicine and pharmacology.

For example, Patent Publication 1 has reported that cyclic dipeptides having 2,5-diketopiperazine structures have anti-depressant action, action for improving learning motivation or the like. Also, Non-Patent Publication 1 describes that a cyclic dipeptide Cyclo(His-Pro) shows diversified physiological activities, including actions involving the central nervous system, such as lowering of body temperature and suppression of appetite; and hormone-like actions such as inhibition of prolactin secretion and promotion of growth hormone secretion, and the publication also reports that a cyclic dipeptide Cyclo(Leu-Gly) shows actions for improving memory functions, and that a cyclic dipeptide Cyclo(Asp-Pro) shows an action of inhibiting fat preference. Non-Patent Publication 2 has reported cyclic dipeptides having an anti-bacterial action and an anti-oxidative action.

In addition, Non-Patent Publication 3 describes that a cyclic dipeptide Cyclo(Trp-Pro) has an anti-cancer action, that cyclic dipeptides Cyclo(His-Pro) and Cyclo(Gly-Pro) have an anti-bacterial action, that a cyclic dipeptide Cyclo(His-Pro) has a neuroprotectant action, that a cyclic dipeptide Cyclo(Gly-Pro) has an action for improving memory functions, and that cyclic dipeptides Cyclo(Tyr-Pro) and Cyclo(Phe-Pro) have an action as a biological herbicide.

PRIOR ART REFERENCES

Patent Publications

Patent Publication 1: Japanese Unexamined Patent Publication No. 2012-517998

Non-Patent Publications

Non-Patent Publication 1: *Peptides*, 16(1), 151-164 (1995)
Non-Patent Publication 2: *Biosciences and Industries*, 60(7), 454-457 (2002)
Non-Patent Publication 3: *Chemical Reviews*, 112, 3641-3716 (2012)

SUMMARY OF THE INVENTION

Problems to be Solved by the Invention

However, there are many functions not yet elucidated for cyclic dipeptides.

An object of the present invention is to provide a uric acid-lowering agent containing, as an active ingredient, a cyclic dipeptide having an excellent action of lowering a uric acid level; a uric acid-lowering agent containing, as an active ingredient, a composition containing the cyclic dipeptide; and a xanthine oxidase inhibitor containing the cyclic dipeptide as an active ingredient.

Means to Solve the Problems

The present invention relates to the following [1] to [9]:

[1] a uric acid-lowering agent containing, as an active ingredient, a tyrosine-containing cyclic dipeptide selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or a salt thereof;

[2] a uric acid-lowering agent containing, as an active ingredient, a composition containing a tyrosine-containing cyclic dipeptide selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or a salt thereof;

[3] a composition for lowering a uric acid level, containing one or more tyrosine-containing cyclic dipeptides selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or salts thereof;

[4] a xanthine oxidase inhibitor containing, as an active ingredient, a tyrosine-containing cyclic dipeptide selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or a salt thereof;

[5] a xanthine oxidase inhibitor containing, as an active ingredient, a composition containing a tyrosine-containing cyclic dipeptide selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or a salt thereof;

[6] a composition for inhibiting a xanthine oxidase, containing one or more tyrosine-containing cyclic dipeptides selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or a salt thereof;

[7] one or more tyrosine-containing cyclic dipeptides selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or salts thereof, for use in lowering a uric acid level;

[8] use of one or more tyrosine-containing cyclic dipeptides selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or salts thereof, for lowering a uric acid level;

[9] a method for lowering a uric acid level, including the step of administering an effective amount of one or more tyrosine-containing cyclic dipeptides selected from the group consisting of cyclotryptophanyltyrosine, cycloseryltyrosine, cycloprolyltyrosine, cyclotyrosylglycine, cyclotyrosyltyrosine, cyclophenylalanyltyrosine, cycloleucyltyrosine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or salts thereof to an individual in need of lowering a uric acid level.

Effects of the Invention

The uric acid-lowering agent of the present invention exhibits an excellent effect of having an excellent action of lowering a uric acid level.

MODES FOR CARRYING OUT THE INVENTION

The uric acid-lowering agent of the present invention is characterized in that the uric acid-lowering agent contains, as an active ingredient, a cyclic dipeptide selected from the group consisting of cyclotryptophanyltyrosine [Cyclo(Trp-Tyr)], cycloseryltyrosine [Cyclo(Ser-Tyr)], cycloprolyltyrosine [Cyclo(Pro-Tyr)], cyclotyrosylglycine [Cyclo(Tyr-Gly)], cyclotyrosyltyrosine [Cyclo(Tyr-Tyr)], cyclophenylalanyltyrosine [Cyclo(Phe-Tyr)], cycloleucyltyrosine [Cyclo(Leu-Tyr)], cyclolysyltyrosine [Cyclo(Lys-Tyr)], cyclohistidyltyrosine [Cyclo(His-Tyr)], cycloalanyltyrosine [Cyclo(Ala-Tyr)], cycloglutamyltyrosine [Cyclo(Glu-Tyr)], cyclovalyltyrosine [Cyclo(Val-Tyr)], cycloisoleucyltyrosine [Cyclo(Ile-Tyr)], cyclothreonyltyrosine [Cyclo(Thr-Tyr)], cycloaspartyltyrosine [Cyclo(Asp-Tyr)], cycloasparaginyltyrosine [Cyclo(Asn-Tyr)], cycloglutaminyltyrosine [Cyclo(Gln-Tyr)], cycloarginyltyrosine [Cyclo(Arg-Tyr)], cyclomethionyltyrosine[Cyclo(Met-Tyr)], and cyclotyrosylcysteine [Cyclo(Tyr-Cys)], or salts thereof, the cyclic dipeptide containing tyrosine. The above tyrosine-containing cyclic dipeptide may be hereinafter referred to as the cyclic dipeptide of the present invention or the diketopiperazine of the present invention. Here, in the present specification, so long as the constitution of the amino acids in the cyclic dipeptides is the same, it does not matter which amino acids are written first. For example, Cyclo(Trp-Tyr) and Cyclo(Tyr-Trp) are the same cyclic dipeptide.

The cyclic dipeptide of the present invention may be any one so long as at least one of the constituting amino acids is tyrosine. For example, in a case where the two constituting amino acids are named an amino acid A and an amino acid B, the cyclic dipeptide has a structure such that a carboxy group of the amino acid A and an amino group of the amino acid B may be subjected to dehydration condensation, and an amino group of the amino acid A and a carboxy group of the amino acid B are subjected to dehydration condensation. The cyclic dipeptide of the present invention as described above contains tyrosine as a constituent. Although the detailed reasons are not elucidated, in consideration of the matters that the phenylalanine-containing cyclic dipeptide having the same aromatic ring is not confirmed to have an action of inhibiting a xanthine oxidase according to the comparison made between Tables 1 and 3 given later, it is assumed that the activity of a xanthine oxidase is inhibited by a phenolic hydroxyl group of the tyrosine. However, these assumptions are not construed to limit the present invention.

The uric acid-lowering agent of the present invention may be any ones so long as the uric acid-lowering agent contains, as an active ingredient, one or more cyclic dipeptides among the twenty cyclic dipeptides listed above or salts thereof. Therefore, one embodiment of the present invention includes a uric acid-lowering agent containing, as an active ingredient, a composition containing a cyclic dipeptide selected from the twenty cyclic dipeptides listed above or a salt thereof. Among them, from the viewpoint of the effects of inhibiting a xanthine oxidase, as the cyclic dipeptide used as an active ingredient, one or more cyclic dipeptides selected from the group consisting of cycloseryltyrosine, cyclotyrosylglycine, cyclotyrosyltyrosine, cyclophenylalanyltyrosine, cycloleucyltyrosine, cyclovalyltyrosine, cycloisoleucyltyrosine, cycloaspartyltyrosine, cycloasparaginylty­rosine, cycloarginyltyrosine, cyclomethionyltyrosine, and cyclotyrosylcysteine, or salts thereof are preferably contained; one or more cyclic dipeptides selected from the group consisting of cyclotyrosylglycine, cyclotyrosyltyrosine, cyclophenylalanyltyrosine, cycloleucyltyrosine, cyclovalyltyrosine, cycloisoleucyltyrosine, cyclomethionyltyrosine, and cyclotyrosylcysteine, or salts thereof are more preferably contained; one or more cyclic dipeptides selected from the group consisting of cyclotyrosyltyrosine, cyclophenylalanyltyrosine, and cycloleucyltyrosine or salts thereof are even more preferably contained; and cyclotyrosyltyrosine or a salt thereof is even more preferably contained.

Among the cyclic dipeptides constituting the uric acid-lowering agent of the present invention, the ratio of a total amount occupied by cyclotyrosyltyrosine, cyclophenylalanyltyrosine, and cycloleucyltyrosine and salts thereof having high action of inhibiting xanthine oxidase is preferably 5% by weight or more, more preferably 10% by weight or more, and even more preferably 15% by weight or more, from the viewpoint of effects of inhibiting a xanthine oxidase. In addition, although the upper limit is not particularly limited, the total amount is preferably 90% by weight or less, and more preferably 60% by weight or less, from the viewpoint of solubilization property.

In addition, a weight ratio of cyclophenylalanyltyrosine to cyclotyrosyltyrosine, i.e. Cyclo(Tyr-Phe)/Cyclo(Tyr-Tyr), is preferably from 95/5 to 35/65, more preferably from 90/10 to 40/60, and even more preferably from 90/10 to 50/50, from the viewpoint of the effects of inhibiting a xanthine oxidase.

In addition, a weight ratio of cyclophenylalanyltyrosine to cyclotyrosylglycine, i.e. Cyclo(Phe-Tyr)/Cyclo(Tyr-Gly), is preferably from 90/10 to 30/70, more preferably from 90/10 to 40/60, and even more preferably from 90/10 to 50/50, from the viewpoint of the effects of inhibiting a xanthine oxidase.

The salts of the cyclic dipeptide as used herein refer to any optional pharmacologically acceptable salts of the above-mentioned cyclic dipeptides, including inorganic salts and organic salts, and the salts include, for example, sodium salts, potassium salts, calcium salts, magnesium salts, ammonium salts, hydrochlorides, sulfates, nitrates, phosphates, salts of organic acids (acetates, citrates, maleates, malates, oxalates, lactates, succinates, fumarates, propionates, formates, benzoates, picrates, benzenesulfonates, and the like), and the like of the above cyclic dipeptides.

The cyclic dipeptide of the present invention can be prepared in accordance with a method known in the art. For example, the cyclic dipeptide may be produced by a chemical synthesis method, an enzyme method, or a microbial fermentation method, or the cyclic dipeptide may be synthesized by subjecting a linear peptide to dehydration and cyclization reaction, or the cyclic dipeptide can also be prepared in accordance with a method described in Japanese Patent Laid-Open No. 2003-252896 or *J. Peptide Sci.*, 10, 731-737 (2004). In the present invention, a treated product obtained by subjecting a solution containing a soybean peptide to a heat treatment can be suitably used. Accordingly, for example, a uric acid-lowering agent containing, as an active ingredient, a treated product obtained by subjecting a solution containing a soybean peptide to a heat treatment can be provided, as a composition containing the cyclic dipeptide or a salt thereof of the present invention.

The treated product obtained by subjecting a solution containing a soybean peptide to a heat treatment refers specifically to one that can be prepared, for example, by dissolving a soybean peptide in water at a concentration of from 20 to 500 mg/mL, and heating the solution under the conditions of from 40° to 150° C. for 5 minutes to 120 hours. The treated product obtained may be subjected to a treatment such as filtration, centrifugation, concentration, ultrafiltration, lyophilization, or powdering as desired.

The salt of the cyclic dipeptide can be easily prepared by one of ordinary skill in the art in accordance with any methods that are known in the art.

The cyclic dipeptide or a salt thereof of the present invention obtained as mentioned above can be used for inhibiting the activity of a xanthine oxidase, thereby controlling the generation of uric acid. Accordingly, the present invention also provides a xanthine oxidase inhibitor containing, as an active ingredient, a cyclic dipeptide or a salt thereof of the present invention, and a xanthine oxidase inhibitor containing, as an active ingredient, a composition containing a cyclic dipeptide or a salt thereof of the present invention.

Furthermore, the present invention provides a composition characterized in that the composition contains a cyclic dipeptide or a salt thereof of the present invention. Since the composition has the above feature, the composition is capable of inhibiting the activity of a xanthine oxidase, thereby controlling the generation of uric acid, so that the composition can be suitably used as a composition for lowering a uric acid level, or a composition for inhibiting a xanthine oxidase. Therefore, the composition of the present invention is one embodiment of the uric acid-lowering agent, and the composition containing a cyclic dipeptide or a salt thereof is embraced in the present invention.

The uric acid-lowering agent of the present invention is not limited in a dosage form thereof, so long as a cyclic dipeptide or a salt thereof of the present invention migrates in the circulating blood. Here, the dosing or dosage as used herein embraces all the embodiments of administration, ingestion, dosing, and drinking.

The diseases that are in need of administration of a uric acid-lowering agent of the present invention are not particularly limited so long as the diseases are diseases in which some therapeutic effects are observed by lowering a blood uric acid level. The diseases are exemplified by, for example, hyperuricemia, gout, gouty tophus, acute gouty arthritis, chronic gouty arthritis, gouty kidney, urinary calculus, renal dysfunction, joint function disorder, vascular disorder, and the like.

The uric acid-lowering agent of the present invention can also be produced into a formulation in the form of a solid such as a tablet, a granule, a powder, a fine powder, or a capsule, or a liquid such as a common liquid agent, a suspension agent or an emulsion by adding as desired a solvent, a dispersant, an emulsifier, a buffer, a stabilizer, an excipient, a binder, a disintegrant, a lubricant or the like to a cyclic dipeptide or a salt thereof of the present invention in accordance with a known method. In addition, these agents may be administered in accordance with a method of orally ingesting these agents, a method of administration with an injection; or a method of allowing the agents to be absorbed with a percutaneous agent.

In addition, the content of the cyclic dipeptide or a salt thereof of the present invention in the above form is not particularly limited, so long as the content is an amount in which the desired effects of the present invention can be obtained, in consideration of a dosing form, a method of administration or the like. The content of the cyclic dipeptide or a salt thereof of the present invention in the uric acid-lowering agent of the present invention is usually from 1 to 100% by weight or so. Here, the content of the cyclic dipeptide or a salt thereof of the present invention refers to a total amount of the cyclic dipeptide or a salt thereof contained in the uric acid-lowering agent.

The uric acid-lowering agent of the present invention is administered by a suitable method of administration depending upon its form. The method of administration is also not particularly limited so long as a cyclic dipeptide or a salt thereof of the present invention can migrate in the circulating blood, and the uric acid-lowering agent can be administered by, for example, internal ingestion, external application, and an injection. In the case of injection, the uric acid-lowering agent can be administered intravenously, intramuscularly, subcutaneously, and intradermally, and in the case of external applications, the uric acid-lowering agent may be administered by a suitable method of administration as an external preparation such as a suppository.

The dose of the uric acid-lowering agent of the present invention is variable, and may be properly set depending upon the forms, the methods of administration, and the purposes of use, and the age, body weight, and symptoms of human patients or animal patients that are subjects for administration with the uric acid-lowering agent. For example, an effective amount of human ingestion in the present invention of the cyclic dipeptide or a salt thereof of the present invention is preferably 0.2 mg or more, more preferably 2 mg or more, and even more preferably 20 mg or more, and preferably 10 g or less, more preferably 5 g or less, and even more preferably 2 g or less, for 50 kg body weight human per day. In addition, the administration may be performed in a single dose or in a several divided doses in a day within the desired dose range. The period of administration is also optionally chosen. Here, the effective amount of human ingestion of the cyclic dipeptide or a salt thereof of the present invention refers to a total amount of ingestion of the cyclic dipeptide or a salt thereof that shows some effects in human, and the kinds of the cyclic dipeptides are not particularly limited.

The subjects for administration of the uric acid-lowering agent of the present invention as used herein refer preferably to human in need of lowering a blood uric acid level, and the subjects may be also livestock animals such as cattle, horses, and goats; pet animals such as dogs, cats, and rabbits; and experimental animals such as mice, rats, guinea pigs, and monkeys. In addition, the subjects for administration include not only individuals with high blood uric acid levels but also individuals who want to prevent an increase of blood uric acid levels, such as individuals whose blood uric acid levels are not so high but with concerns of increase in blood uric acid levels, individuals who want to prevent hyperuricemia, individuals who want to prevent gout, and individuals who have high levels of intake of foodstuff that increase blood uric acid levels (for example, foodstuff containing purine products such as liver, and fishes and shells such as milts, shrimps, sardines, and bonitos), potential individuals who are considering to ingest the uric acid-lowering agent for physical well-being by seeing the indications that a tyrosine-containing cyclic dipeptide or a soybean peptide heat-treated product is blended.

The present invention also provides a method for lowering a uric acid level, including administering a cyclic dipeptide or a salt thereof of the present invention, or a composition containing a cyclic dipeptide or a salt thereof of the present invention in a therapeutically effective amount to an individual in need of lowering a uric acid level. Here, the individuals in need of lowering a uric acid level are the same as the administration subjects for the uric acid-lowering agent of the present invention mentioned above.

In addition, the therapeutically effective amount as used herein refers to an amount that lowers a uric acid level in a case where a cyclic dipeptide or a salt thereof of the present invention is administered to the above individual, as compared to an individual not administered. A specific effective amount is variable, and may be appropriately set depending upon the dosage forms, the methods of administration, the purposes of use, and age, body weight, symptoms and the like of the individuals.

In the method of treatment of the present invention, a cyclic dipeptide or a salt thereof of the present invention may be administered directly, or as a composition containing a cyclic dipeptide or a salt thereof of the present invention, so as to have the above therapeutically effective amount. In addition, the method of administration is not limited, and the administration can be made by, for example, oral administration.

According to the method of treatment of the present invention, it is possible to lower a blood uric acid level without causing side effects.

EXAMPLES

The present invention will be more particularly described showing Examples, without intending to limit the scope of the present invention to the following Examples.

<Reagents>

As a cyclic dipeptide, one synthesized by KNC Laboratories Co., Ltd. was used. Each of xanthine, Sodium Carboxymethyl Cellulose (CMC-Na), tyrosine (Tyr), formic acid (Special Grade reagent for column chromatography), methanol (used for high-performance liquid chromatography), manufactured by NACALAI TESQUE INC.; each of Allopurinol and potassium oxonate, manufactured by Wako Pure Chemical Industries, Ltd.; xanthine oxidase, manufactured by TOYOBO CO., LTD.; Xanthine Oxidase Assay Kit, manufactured by Cayman Chemical Company; L-Tyrosyl-glycine, manufactured by Santa Cruz Biotechnology Inc.; Glycyl-L-tyrosine, manufactured by Sigma-Aldrich; each of Tissue Protein Extraction Reagent (T-PER), Protease inhibitor cocktail kit, Pierce BCA protein assay kit, and polystyrene Black 96-well plate manufactured by Thermo Scientific; heparin sodium manufactured by MOCHIDA PHARMACEUTICAL CO., LTD.; Pravastatin sodium, manufactured by SIGMA; a soybean peptide (Hinute AM), manufactured by FUJI OIL, CO., LTD., were respectively used.

<Statistical Analysis>

In the subsequent Test Examples, data were indicated as mean±standard error. As a statistical test, in Test Example 1 a Student's t-test was used, and in other Test Examples dispersion analysis was performed with a one-way ANOVA, and thereafter a multiple comparison test was carried out using Dunnet's test. In the results the denotation "*" means a significant difference p<0.05, and the denotation "†" means a significant difference p<0.1. Here, all these analyses were performed using SPSS for Windows(Registered Trademark) Release 17.0, Manufactured by SPSS.

Test Example 1

Studies on in vitro XO Inhibiting Action

The in vitro xanthine oxidase (XO) inhibiting action was studied on 210 kinds of cyclic dipeptides, linear dipeptides Tyr-Gly and Gly-Tyr, and an amino acid Tyr.

Concretely, 75 µL of 4 U/L xanthine oxidase (XO) dissolved in a phosphate buffer (PBS), pH 7.5, was dispensed in each of the wells of a 96-well plate, and 5 µL of a sample solution was added thereto so that a peptide or amino acid had a given concentration based on the final XO concentration, and the mixture was mixed for 5 minutes (a final concentration of a peptide or amino acid being from 50 to 500 µM). Thereafter, 20 µL of a 250 µM xanthine solution previously dissolved in the PBS was added thereto, and the absorbance after 30 minutes was measured using a spectrophotometer (Synegy HT, manufactured by Bio Tek). The XO inhibition rate (%) at each concentration was calculated by the following calculation formula, to obtain activities of inhibiting XO ($IC_{50}$ values). Table 1 shows activities of inhibiting a xanthine oxidase ($IC_{50}$ values) of 12 kinds of Tyr-containing cyclic dipeptides, Table 2 shows xanthine oxidase inhibition rates (%) of 8 kinds of Tyr-containing cyclic dipeptides at a concentration of 100 µM, and Table 3 shows activities of inhibiting a xanthine oxidase ($IC_{50}$ values) of 20 kinds of Phe-containing cyclic dipeptides. Here, as a positive control, a known uric acid-lowering agent Allopurinol ($IC_{50}$ value: 12.5 µM) was utilized.

$$\% \text{ Inhibition} = \left\{ \frac{(A-B)-(C-D)}{A-B} \right\} \times 100$$

wherein A: the absorbance of an enzyme-added, sample-non-added group at 295 nm;
B: the absorbance of an enzyme-non-added, sample-non-added group at 295 nm;
C: the absorbance of an enzyme-added, sample-added group at 295 nm; and
D: the absorbance of an enzyme-non-added, sample-added group at 295 nm.

TABLE 1

Activity of Inhibiting XO (Xanthine Oxidase) of Tyr(Tyrosine)-Containing Cyclic Dipeptides

| Compound | $IC_{50}$ (µM) |
| --- | --- |
| Cyclo(Ser-Tyr) | 188.9 ± 52.5 |
| Cyclo(Tyr-Gly) | 49.0 ± 3.0 |
| Cyclo(Tyr-Tyr) | 29.5 ± 2.9 |
| Cyclo(Phe-Tyr) | 22.2 ± 0.8 |
| Cyclo(Leu-Tyr) | 23.8 ± 5.3 |
| Cyclo(Val-Tyr) | 79.4 ± 16.1 |
| Cyclo(Ile-Tyr) | 86.7 ± 2.8 |
| Cyclo(Asp-Tyr) | 172 ± 13.5 |
| Cyclo(Asn-Tyr) | 113 ± 11.4 |
| Cyclo(Arg-Tyr) | 211 ± 36.2 |
| Cyclo(Met-Tyr) | 56.4 ± 2.9 |
| Cyclo(Tyr-Cys) | 77.2 ± 4.7 |

TABLE 2

Activity of Inhibiting XO (Xanthine Oxidase) of Tyr(Tyrosine)-Containing Cyclic Dipeptides

| Compound | Inhibition Rate (%) at Concentration of 100 µM |
| --- | --- |
| Cyclo(Trp-Tyr) | 19.1 |
| Cyclo(Pro-Tyr) | 2.3 |
| Cyclo(Lys-Tyr) | 25.7 |
| Cyclo(His-Tyr) | 3.2 |
| Cyclo(Ala-Tyr) | 8.3 |
| Cyclo(Glu-Tyr) | 0.4 |
| Cyclo(Thr-Tyr) | 2.6 |
| Cyclo(Gln-Tyr) | 42.6 |

TABLE 3

Activity of Inhibiting XO (Xanthine Oxidase) of Phe(Phenylalanine)-Containing Cyclic Dipeptides

| Compound | $IC_{50}$ (µM) |
| --- | --- |
| Cyclo(Trp-Phe) | >100 |
| Cyclo(Ser-Phe) | >300 |
| Cyclo(Pro-Phe) | >100 |
| Cyclo(Phe-Gly) | >100 |
| Cyclo(Phe-Tyr) | 22.2 ± 0.8 |
| Cyclo(Phe-Phe) | >100 |
| Cyclo(Leu-Phe) | >100 |
| Cyclo(Lys-Phe) | >300 |
| Cyclo(His-Phe) | >100 |
| Cyclo(Ala-Phe) | >100 |
| Cyclo(Glu-Phe) | >100 |
| Cyclo(Val-Phe) | 60.5 ± 2.4 |
| Cyclo(Ile-Phe) | >100 |
| Cyclo(Thr-Phe) | >300 |
| Cyclo(Asp-Phe) | >300 |
| Cyclo(Asn-Phe) | >300 |
| Cyclo(Gln-Phe) | >300 |
| Cyclo(Arg-Phe) | >300 |
| Cyclo(Met-Phe) | >100 |
| Cyclo(Phe-Cys) | 132.8 ± 25.2 |

It can be seen from Tables 1 and 2 that the Tyr-containing cyclic dipeptides have activities of inhibiting an XO, and from Table 3 that the activities of inhibiting an XO are attenuated when Tyr is replaced by Phe.

Also, the XO inhibition rates (%) were measured for Cyclo(Tyr-Gly), linear dipeptides Tyr-Gly and Gly-Tyr, and an amino acid Tyr in the same manner. The results are shown in FIG. 1.

Figure 1:
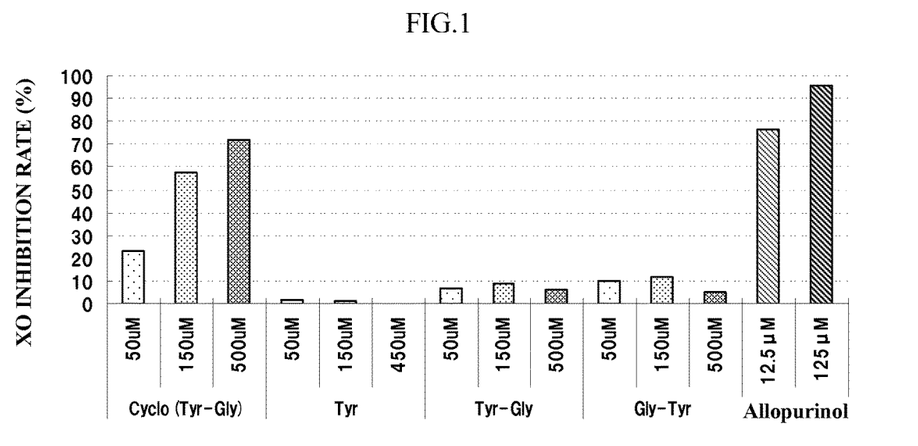
FIG. 1 is a diagram showing xanthine oxidase inhibition rates (%) of Cyclo(Tyr-Gly), linear dipeptides Tyr-Gly and Gly-Tyr, and an amino acid Tyr.

It can be seen from FIG. 1 that the activity of inhibiting an XO is exhibited by cyclization, suggesting that a cyclic dipeptide is important.

Test Example 2

Studies on Actions of Lowering Serum Uric Acid Levels for Hyperuricemic Mice

The actions of lowering serum uric acid levels with cyclic dipeptides were studied in hyperuricemic model animals.

As to the animals used, male 7-week old BALBc mice were purchased from CLEA Japan, Inc., and subjected to an experiment after a one-week period of conditioning. The animals were bred in a breeding room with air-conditioning facilities (temperature: 23.5°±1.0° C., humidity: 55±10 RH %, the number of ventilation: 12 to 15 times/hour, illuminated: from 7:00 to 19:00 each day). During the period of conditioning, the mice were allowed to take a commercially available feed (CE-2, manufactured by CLEA Japan, Inc.) and distilled water ad libitum.

Oxonic acid is a substance that raises a blood uric acid level by inhibiting a urikase, a metabolic enzyme for uric acid. In view of the above, potassium oxonate (PO) was administered, thereby generating hyperuricemic model animals (see, *Planta Med* 2009; 75:302-306). Studies were made on the following 6 groups:
1) normal group (Normal Group, without loading oxonic acid);
2) group administered with PO (PO Group, with loading oxonic acid);
3) group administered with PO+Allopurinol 1 mg/kg (PO+ AL Group);
4) group administered with PO+Cyclo(Tyr-Gly) 10 mg/kg (PO+CTG 10 Group);
5) group administered with PO+Cyclo(Tyr-Gly) 30 mg/kg (PO+CTG 30 Group); and
6) group administered with PO+Cyclo(Tyr-Gly) 100 mg/kg (PO+CTG 100 Group), wherein in each group, n=6 to 8. In all the groups that include PO administration, PO previously suspended in a 0.5% aqueous CMC-Na solution was administered at a concentration of 250 mg/kg, and Normal Group was administered with a 0.5% aqueous CMC-Na solution, each being administered intraperitoneally. Next, after one hour, the group administered with PO+Allopurinol was administered with 1 mg/kg Allopurinol, each of the groups administered with PO+Cyclo(Tyr-Gly) was administered with Cyclo(Tyr-Gly) at 10, 30, or 100 mg/kg, and Normal Group was administered with distilled water, each being administered orally. After 2 hours from the administration with PO, the blood was collected from the abdominal vena cava under anesthesia. After blood removal, the liver was harvested. The collected blood was allowed to stand at room temperature for 45 minutes, and centrifuged at 8,000 rpm for 10 minutes to recover sera. Here, the sera and the liver were preserved at −80° C. until the measurements were carried out.

The serum uric acid level was measured using 7180 Clinical Analyzer (manufactured by Hitachi Technologies). The results are shown in FIG. 2.

Figure 3:
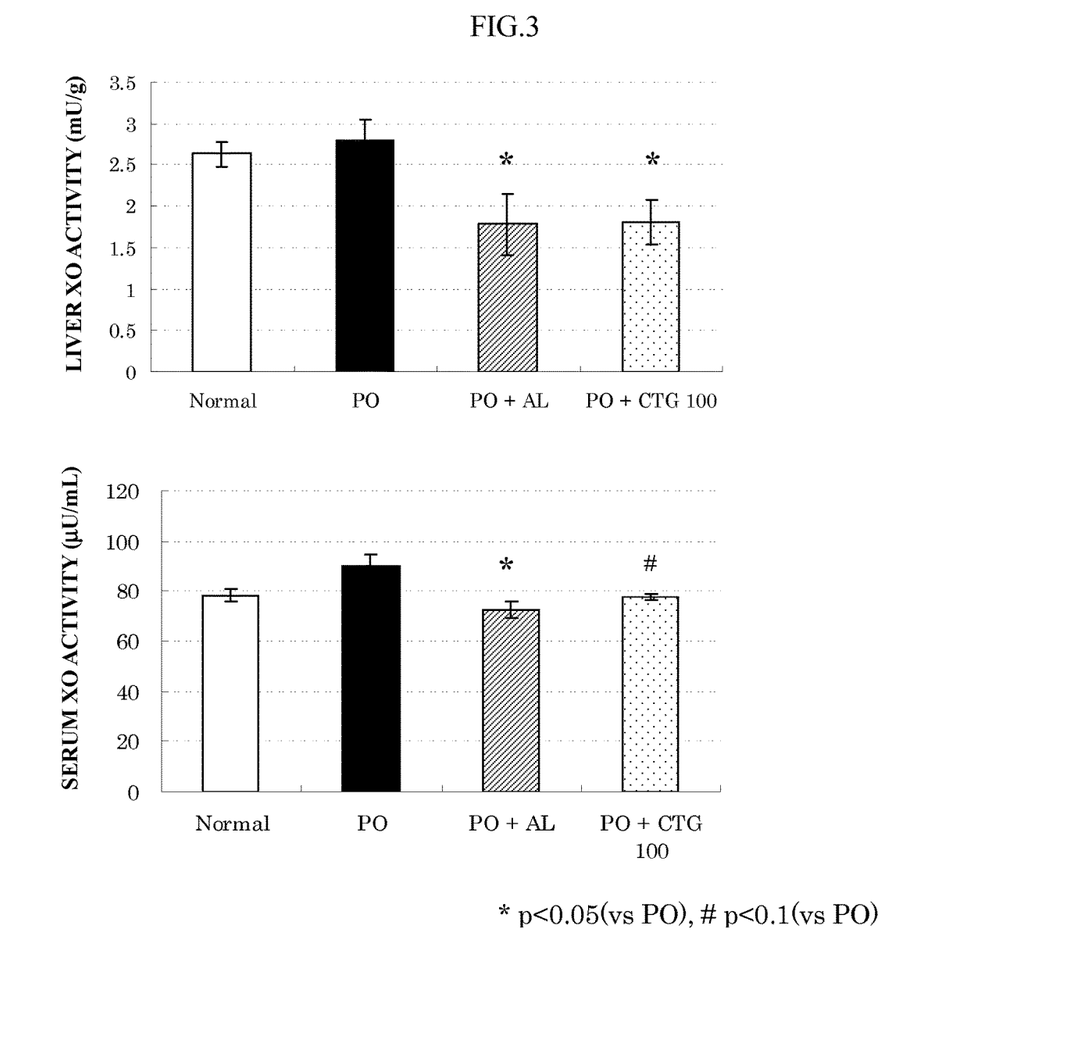
FIG. 3 is a diagram showing the results of studies on actions of inhibiting xanthine oxidase (XO) activity of tyrosine-containing cyclic dipeptides for hyperuricemic mice, wherein the upper panel is a diagram showing XO activity in the liver, and the lower panel is a diagram showing XO activity in the sera.

Next, the livers of mice were added to a mixture of an ice-cooled protease inhibitor cocktail and an EDTA-containing tissue protein extraction reagent (T-PER), and homogenized, and the homogenate was then centrifuged at 15,000 rpm, at 4° C. for 15 minutes, and the collected supernatant was subjected to an assay for a xanthine oxidase (XO) activity. The XO activities in the livers and the sera were assayed using a xanthine oxidase assay kit and a polystyrene Black 96-well plate. Concretely, XO standard samples, liver samples, or sera samples were added in an amount of 50 μL, and thereafter 50 μL, of an analytical cocktail prepared by mixing an assay buffer, a Detector and HRP in a mass ratio of 98/1/1 was added thereto. The mixture was allowed to react at 37° C. for 45 minutes while shading light, and a fluorescence was then measured at an excitation wavelength of from 520 to 550 nm and an emission wavelength of from 585 to 595 nm with a spectrophotometer (Synegy HT, manufactured by Bio Tek). The sera XO activities were indicated in units of mU/mL, and the XO activities in the liver were indicated in units of mU/mg, using the results of assaying a protein concentration with a Pierce BCA protein assay kit. The results are shown in FIG. 3.

Figure 2:
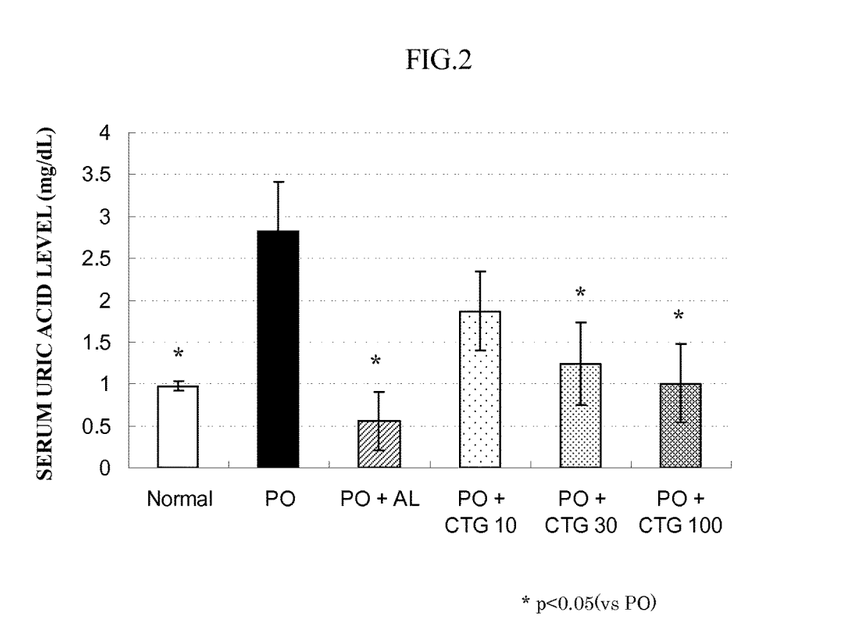
FIG. 2 is a diagram showing the results of studies on the actions of lowering serum uric acid levels of tyrosine-containing cyclic dipeptides for hyperuricemic mice.

It can be seen from FIG. 2 that Cyclo(Tyr-Gly) has an action of lowering a uric acid level in a dose-dependent manner, and that the group administered with Cyclo(Tyr-Gly) 30 or 100 mg/kg has a significant difference in effects on the PO Group, in the same manner as the group administered with Allopurinol. In addition, it can be seen from FIG. 3 that the xanthine oxidase activities in the liver and in the sera are inhibited in the group administered with Cyclo (Tyr-Gly) 100 mg/kg, in the same manner as the group administered with Allopurinol 1 mg/kg.

Test Example 3

Studies on Action of Lowering Serum Uric Acid Levels of Soybean Peptide Heat-Treated Products for Hyperuricemic Mice The actions of lowering serum uric acid levels of soybean peptide heat-treated products were studied using hyperuricemic model animals, in the same manner as in Test Example 2. Concretely, the animals used were furnished in the same manner as in Test Example 2, and studies were made on the following 5 groups.
1) normal group (Normal Group, without loading oxonic acid);
2) group administered with PO (PO Group, with loading oxonic acid);
3) group administered with PO+Allopurinol 1 mg/kg (PO+ AL Group);
4) group administered with PO+soybean peptide heat-treated product 2 g/kg; and
5) group administered with PO+mixture of 8 kinds of Tyr-containing cyclic dipeptides 11 mg/kg, wherein in each group, n=6 to 7.

Figure 4:
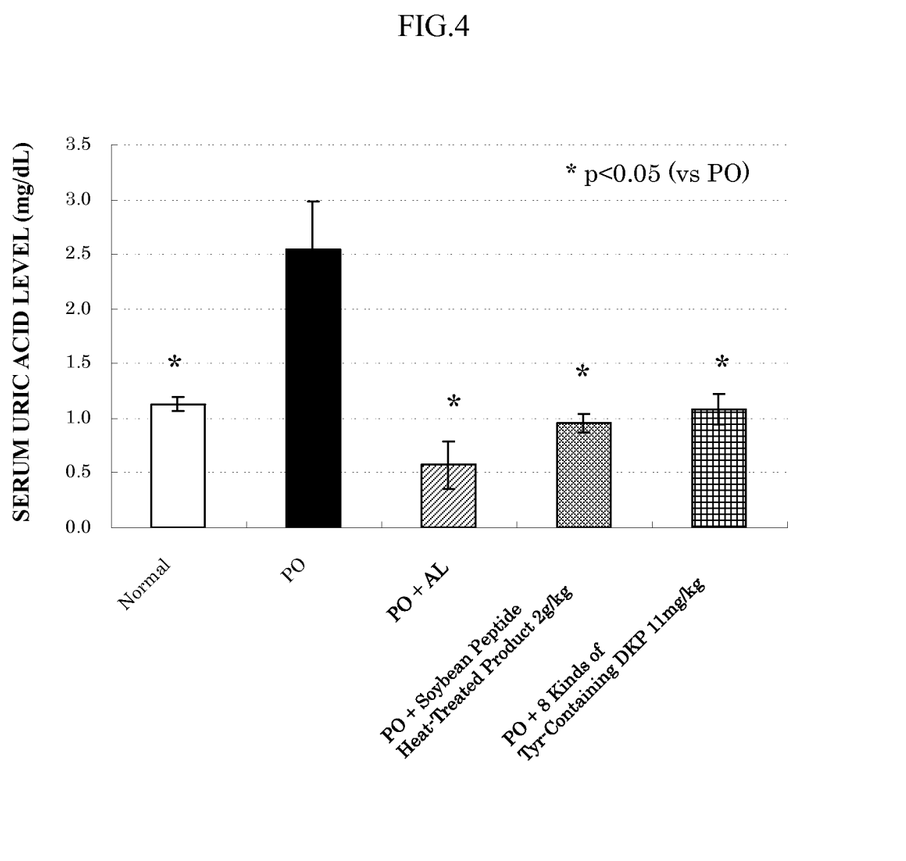
FIG. 4 is a diagram showing the results of studies on actions of lowering serum uric acid levels of soybean peptide heat-treated product, and a mixture of 8 kinds of Tyr-containing cyclic dipeptides contained in the soybean peptide heat-treated product for hyperuricemic mice.

For each of the above-mentioned groups, the administration and the blood collection were carried out in the same manner as in Test Example 2 to measure a serum uric acid level. The results are shown in FIG. 4. Here, the mixture of the 8 kinds of cyclic dipeptides prepared by using synthesized products of Cyclo(Ser-Tyr), Cyclo(Tyr-Gly), Cyclo(Tyr-Tyr), Cyclo (Phe-Tyr), Cyclo(Leu-Tyr), Cyclo(Val-Tyr), Cyclo(Ile-Tyr), and Cyclo(Asn-Tyr), in amounts to be contained in the soybean peptide heat-treated product, was used.

Here, the heat-treated product of the soybean peptide obtained by dissolving a soybean peptide (Hinute AM, manufactured by FUJI OIL, CO., LTD.) in distilled water in a concentration of 200 mg/mL, heating to 132° C. for 3 hours, and lyophilizing the heated mixture was used. The content of the cyclic dipeptide of the soybean peptide heat-treated product was measured according to LC-MS/MS under the following conditions. Here, Cyclo(Tyr-Cys) could not be determined because the standard product was unstable in an aqueous solution. The results are shown in Table 4.

[LC-MS/MS Analytical Conditions]

| | |
|---|---|
| LC Apparatus | SHIMADZU UFLC XR |
| Column | Agilent technologies, Zorbax SB-AQ, 1.8 μm, 21 mm × 150 mm |
| Column Temperature | 40° C. |
| Mobile Phase | Gradient Analyses of A: 0.1% formic acid, and B: methanol |
| Flow Rate | 0.2 mL/min |
| Amount Injected | 2 μL |
| Detector | AB Sciex 4000 Q TRAP-Turbo Spray (ESI)-Scheduled MRM (multiple reaction monitoring) |

TABLE 4

| Cyclic Dipeptide | Content ($\times 10^3$ ppm) |
|---|---|
| Cyclo(Trp-Tyr) | 0.10 |
| Cyclo(Ser-Tyr) | 1.06 |
| Cyclo(Pro-Tyr) | 0.53 |
| Cyclo(Tyr-Gly) | 0.47 |
| Cyclo(Tyr-Tyr) | 0.18 |
| Cyclo(Phe-Tyr) | 0.74 |
| Cyclo(Leu-Tyr) | 0.92 |

TABLE 4-continued

| Cyclic Dipeptide | Content (×10³ ppm) |
|---|---|
| Cyclo(Lys-Tyr) | 1.25 |
| Cyclo(His-Tyr) | 0.32 |
| Cyclo(Ala-Tyr) | 0.52 |
| Cyclo(Glu-Tyr) | 0.22 |
| Cyclo(Val-Tyr) | 0.23 |
| Cyclo(Ile-Tyr) | 1.02 |
| Cyclo(Thr-Tyr) | 0.73 |
| Cyclo(Asp-Tyr) | 0.23 |
| Cyclo(Asn-Tyr) | 0.73 |
| Cyclo(Gln-Tyr) | 0.39 |
| Cyclo(Arg-Tyr) | 1.34 |
| Cyclo(Met-Tyr) | 0.17 |
| Cyclo(Tyr-Cys) | Undeterminable |

It can be seen from Table 4 and FIG. 4 that the soybean peptide heat-treated product contains a cyclic dipeptide of the present invention, and has an excellent action of lowering a blood uric acid level.

Test Example 4

Studies on Effective Amount of Soybean Peptide Heat-Treated Products for Hyperuricemic Mice The actions of lowering serum uric acid levels of soybean peptide heat-treated products according to dose were studied using hyperuricemic model animals, in the same manner as in Test Example 3. Concretely, the animals used were furnished in the same manner as in Test Example 2, and studies were made on the following 6 groups.
1) normal group (Normal Group, without loading oxonic acid);
2) group administered with PO (PO Group, with loading oxonic acid);
3) group administered with PO+Allopurinol 1 mg/kg (PO+ AL Group);
4) group administered with PO+soybean peptide heat-treated product 200 mg/kg;
5) group administered with PO+soybean peptide heat-treated product 400 mg/kg; and
6) group administered with PO+soybean peptide heat-treated product 800 mg/kg,
wherein in each group, n=5 to 6. For each of the above-mentioned groups, the administration and the blood collection were carried out in the same manner as in Test Example 2 to measure a serum uric acid level. The results are shown in FIG. 5.

Figure 5:
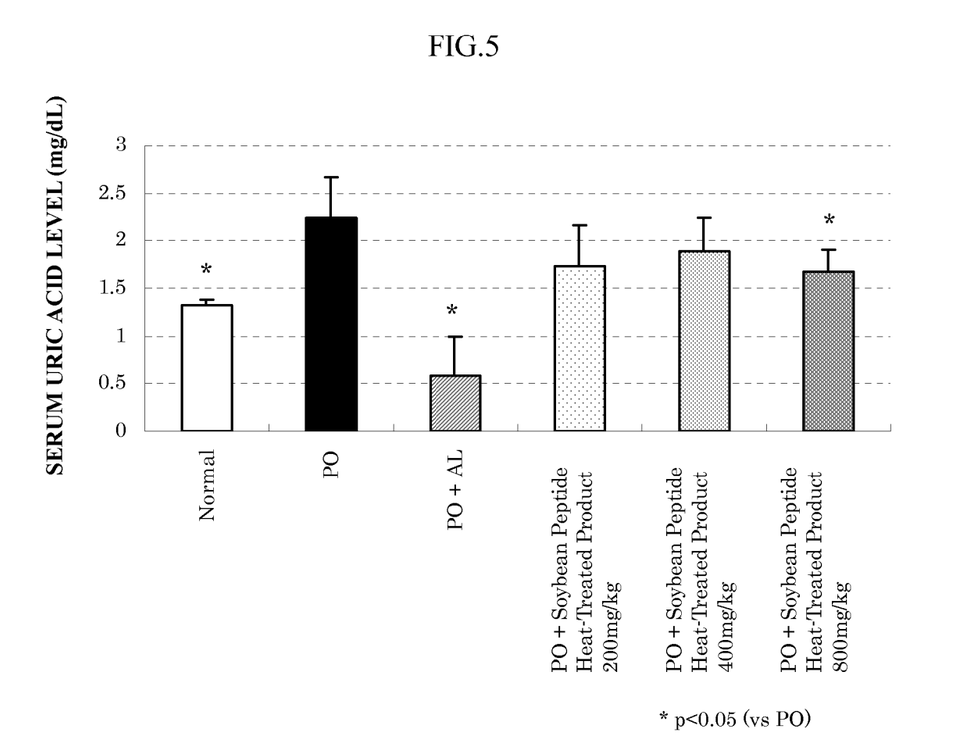
FIG. 5 is a diagram showing the results of studies on serum uric acid according to the dosages of the soybean peptide heat-treated products for hyperuricemic mice.

It can be seen from FIG. 5 that the soybean peptide heat-treated product is found to have a significant difference against the uric acid level of hyperuricemic model mice by administering the soybean peptide heat-treated product at 800 mg/kg.

The cyclic dipeptide of the present invention can be prepared even from materials derived from foods, and the cyclic dipeptide is a material that is comfortably ingestible and has safety, so that the cyclic dipeptide has an advantage different from Allopurinol, which has some concerns in side effects. Although the cyclic dipeptide of the present invention might differ in the extent of actions depending upon the amounts used, the cyclic dipeptide is found to have actions of lowering a uric acid level that are equivalent or milder than that of Allopurinol depending upon the amounts used. The lowering of uric acid levels must be dealt over a long period of time together with dietary therapy, so that those having milder actions are said to be rather preferable, from the viewpoint of daily intake.

INDUSTRIAL APPLICABILITY

The uric acid-lowering agent of the present invention has an excellent an action of lowering a uric acid level, and the uric acid-lowering agent is useful in, for example, prevention or treatment of hyperuricemia, gout or the like.

The invention claimed is:

1. A composition for lowering a uric acid level, comprising a uric acid-lowering agent, wherein the uric acid-lowering agent comprises one or more tyrosine-comprising cyclic dipeptides selected from a first group consisting of cyclotyrosyltyrosine, cyclophenylalanyltyrosine and cycloleucyltyrosine, or salts thereof, and one or more tyrosine-comprising cyclic dipeptides selected from a second group consisting of cyclotryptophanyltyrosine, cycloseryltyrosine, cycloprolyltyrosine, cyclotyrosylglycine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or salts thereof, and
    wherein a total amount of the tyrosine-comprising cyclic dipeptides from the first group in the uric acid-lowering agent is from 5% by weight to 90% by weight relative to a total amount of the uric acid-lowering agent, so that the tyrosine-comprising cyclic dipeptides from the first group are present in an effective amount for lowering the uric acid level,
    wherein the one or more tyrosine-comprising cyclic dipeptides from the first group comprises cyclophenylalanyltyrosine, and the one or more tyrosine-comprising cyclic dipeptides from the second group comprises cyclotyrosylglycine, and
    wherein a ratio of cyclophenylalanyltyrosine to cyclotyrosylglycine is from 90/10 to 30/70.

2. The composition for lowering a uric acid level according to claim 1, wherein the composition is a treated product obtained by heat-treating a solution comprising a soybean peptide.

3. A composition for inhibiting a xanthine oxidase comprising a xanthine oxidase inhibitor, wherein the xanthine oxidase inhibitor comprises one or more tyrosine-comprising cyclic dipeptides selected from a first group consisting of cyclotyrosyltyrosine, cyclophenylalanyltyrosine, and cycloleucyltyrosine, or salts thereof, and one or more tyrosine-comprising cyclic dipeptides selected from a second group consisting of cyclotryptophanyltyrosine, cycloseryltyrosine, cycloprolyltyrosine, cyclotyrosylglycine, cyclolysyltyrosine, cyclohi stidyltyrosine, cycloalanyltyrosine, cycloglutamyltyrosine, cyclovalyltyrosine, cycloi soleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or salts thereof, and
    wherein a total amount of the tyrosine-comprising cyclic dipeptides from the first group in the xanthine oxidase inhibitor is from 5% by weight to 90% by weight relative to a total amount of the xanthine oxidase inhibitor, so that the tyrosine-comprising cyclic dipeptides from the first group are present in an effective amount for inhibiting the xanthine oxidase,
    wherein the one or more tyrosine-comprising cyclic dipeptides from the first group comprises cyclophenylalanyltyrosine, and the one or more tyrosine-comprising cyclic dipeptides from the second group comprises cyclotyrosylglycine, and wherein a ratio of cyclophenylalanyltyrosine to cyclotyrosylglycine is from 90/10 to 30/70.

4. The composition for inhibiting a xanthine oxidase according to claim 3, wherein the composition is a treated product obtained by heat-treating a solution comprising a soybean peptide.

5. A method for lowering a uric acid level, comprising the step of administering an effective amount of a composition comprising a uric acid-lowering agent to an individual in need of lowering the uric acid level, wherein the uric acid-lowering agent comprises one or more tyrosine-comprising cyclic dipeptides selected from a first group consisting of cyclotyrosyltyrosine, cyclophenylalanyltyrosine and cycloleucyltyrosine, or salts thereof, and one or more tyrosine-comprising cyclic dipeptides selected from a second group consisting of cyclotryptophanyltyrosine, cycloseryltyrosine, cycloprolyltyrosine, cyclotyrosylglycine, cyclolysyltyrosine, cyclohistidyltyrosine, cycloalanyltyrosine, cycloglutamyltyrosine, cyclovalyltyrosine, cycloisoleucyltyrosine, cyclothreonyltyrosine, cycloaspartyltyrosine, cycloasparaginyltyrosine, cycloglutaminyltyrosine, cycloarginyltyrosine, cyclomethionyltyrosine, and cyclotyrosylcysteine, or salts thereof.

6. The composition for lowering a uric acid level according to claim 1, wherein the one or more tyrosine-comprising cyclic dipeptides from the first group further comprises cyclotyrosyltyrosine, and wherein a ratio of cyclophenylalanyltyrosine to cyclotyrosyltyrosine in the uric acid-lowering agent is from 95/5 to 35/65.

7. The composition for lowering a uric acid level according to claim 1, wherein the total amount of the tyrosine-comprising cyclic dipeptides from the first group in the uric acid-lowering agent is at least 10% by weight relative to the total amount of the uric acid-lowering agent.

8. The composition for lowering a uric acid level according to claim 1, wherein the total amount of the tyrosine-comprising cyclic dipeptides from the first group in the uric acid-lowering agent is at most 60% by weight relative to the total amount of the uric acid-lowering agent.

9. The composition for inhibiting a xanthine oxidase according to claim 3, wherein the one or more tyrosine-comprising cyclic dipeptides from the first group further comprises cyclotyrosyltyrosine, and wherein a ratio of cyclophenylalanyltyrosine to cyclotyrosyltyrosine in the xanthine oxidase inhibitor is from 95/5 to 35/65.

10. The composition for inhibiting a xanthine oxidase according to claim 3, wherein the total amount of the tyrosine-comprising cyclic dipeptides from the first group in the xanthine oxidase inhibitor is at least 10% by weight relative to the total amount of the xanthine oxidase inhibitor.

11. The composition for inhibiting a xanthine oxidase according to claim 3, wherein the total amount of the tyrosine-comprising cyclic dipeptides from the first group in the xanthine oxidase inhibitor is at most 60% by weight relative to the total amount of the xanthine oxidase inhibitor.

12. The method for lowering a uric acid level according to claim 5, wherein the composition is a treated product obtained by heat-treating a solution comprising a soybean peptide.

13. The method for lowering a uric acid level according to claim 5, wherein the one or more tyrosine-comprising cyclic dipeptides from the first group comprises cyclophenylalanyltyrosine and cyclotyrosyltyrosine, and wherein a ratio of cyclophenylalanyltyrosine to cyclotyrosyltyrosine in the uric acid-lowering agent is from 95/5 to 35/65.

14. The method for lowering a uric acid level according to claim 5, wherein the one or more tyrosine-comprising cyclic dipeptides from the first group comprises cyclophenylalanyltyrosine, and the one or more tyrosine-comprising cyclic dipeptides from the second group comprises cyclotyrosylglycine, and wherein a ratio of cyclophenylalanyltyrosine to cyclotyrosylglycine is from 90/10 to 30/70.

15. The method for lowering a uric acid level according to claim 5, wherein the total amount of the tyrosine-comprising cyclic dipeptides from the first group in the uric acid-lowering agent is at least 10% by weight relative to the total amount of the uric acid-lowering agent.

16. The method for lowering a uric acid level according to claim 5, wherein the total amount of the tyrosine-comprising cyclic dipeptides from the first group in the uric acid-lowering agent is at most 60% by weight relative to the total amount of the uric acid-lowering agent.

\* \* \* \* \*